United States Patent
Rodriguez

(10) Patent No.: US 7,297,653 B2
(45) Date of Patent: Nov. 20, 2007

(54) FLUOROPHENYLBORATES AND THEIR USE AS ACTIVATORS IN CATALYST SYSTEMS FOR OLEFIN POLYMERIZATION

(75) Inventor: George Rodriguez, Houston, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 256 days.

(21) Appl. No.: 11/186,238

(22) Filed: Jul. 21, 2005

(65) Prior Publication Data

US 2007/0021575 A1    Jan. 25, 2007

(51) Int. Cl.
*C08F 4/44* (2006.01)
*C07F 5/02* (2006.01)

(52) U.S. Cl. .................. 502/103; 502/152; 502/167; 526/134; 526/348; 568/6

(58) Field of Classification Search .............. 568/6; 502/103, 152, 167; 526/134, 348
See application file for complete search history.

(56) References Cited

U.S. PATENT DOCUMENTS

| | | | |
|---|---|---|---|
| 6,087,460 A * | 7/2000 | Marks et al. | 526/134 |
| 6,248,914 B1 | 6/2001 | Klosin | |
| 6,291,695 B1 | 9/2001 | Marks et al. | |
| 6,541,410 B1 | 4/2003 | Rodriquez | 502/103 |
| 2005/0049436 A1 | 3/2005 | Rodriguez et al. | |

FOREIGN PATENT DOCUMENTS

| | | |
|---|---|---|
| JP | 9-158921 | 6/1997 |
| JP | 10-060034 | 3/1998 |
| WO | 01/81435 | 11/2001 |
| WO | WO03/033545 | 4/2003 |
| WO | WO2004/026923 | 4/2004 |

OTHER PUBLICATIONS

Chen et al., "Sterically Encumbered (Perfluoroaryl) Borane and Aluminate Cocatalysts for Tuning Cation—Anion Ion Pair Structure and Reactivity in Metallocene Polymerization Processes. A Synthetic, Structural, and Polymerization Study", J. Am. Chem. Soc. 1998, 120, pp. 6287-6305.
Sakamoto et al., "Synthesis, Characterization, and Electron-Transport Property of Perfluorinated Phenylene Dendrimers", J. Am. Chem. Soc. 2000, 122, pp. 1832-1833.
Chen et al., "Cocatalysts for Metal-Catalyzed Olefin Polymerization: Activators, Activation Processes, and Structure—Activity Relationships", Chem. Rev. 2000, 100, pp. 1391-1434.
Matsumoto, Kaya et al., "Synthesis of a new, bulky tetraarylphosphonium, a tetraartylboarlborate, and their salt Synthesis of a new, bulky tetraarylphosphonium, a tetraarylborate, and their salt", Synthesis, (13) 2181-2185, 2004.
Newton, Joanna et al., "Synthesis of polysilanes using group IV metallocene based catalysts and unusual boron based co-catalysts", American Chem. Society, Division of Polymer Chemistry Journal, 1998, 39(1), pp. 587-588.

* cited by examiner

*Primary Examiner*—Caixia Lu
(74) *Attorney, Agent, or Firm*—Catherine L. Bell

(57) ABSTRACT

A fluorophenylborate useful as an activator for an olefin polymerization catalyst is represented by the formula:

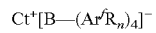

$$Ct^+[B-(Ar^f R_n)_4]^-$$

where $Ct^+$ is a cation capable of extracting an alkyl group from, or breaking a carbon-metal bond of, an organo metallic compound; $Ar^f$ is a fluorophenyl group; n is 1 or 2; and each R is independently selected from a fluorophenyl group and a fluoronaphthyl group, provided that when n=1, each R group is connected at the 3-position relative the connection between the associated $Ar^f$ group and the boron atom and, when n=2; the R groups are connected at the 3-position and the 5-position respectively relative the connection between the associated $Ar^f$ group and the boron atom.

20 Claims, No Drawings

FLUOROPHENYLBORATES AND THEIR USE AS ACTIVATORS IN CATALYST SYSTEMS FOR OLEFIN POLYMERIZATION

FIELD

This invention relates to novel fluorophenylborates and their use as activators in catalyst systems for olefin polymerization.

BACKGROUND

Many catalyst systems for polymerizing olefins, including metallocene and Ziegler-Natta catalyst systems, include an activator or co-catalyst to increase the rate at which the primary catalyst, for example the metallocene complex, polymerizes olefin monomers. An activator may also affect the molecular weight, degree of branching, comonomer content and other properties of the resultant polymer. Typical activators include, for example, alumoxanes, aluminum alkyls and ionizing activators.

Ionizing activators generally include a cation capable of abstracting an alkyl group, or breaking a carbon-metal bond, from the organometallic primary catalyst species together with a charge-balancing noncoordinating or weakly coordinating anion. One known class of ionizing activator are fluorophenylborates and, in particular, perfluorophenylborates, the use of which are reviewed by Eugene at al. in *Chem. Rev.* 2000, 100, page 1391.

Recently, a variety of researchers have investigated the effect of substituting the fluorine atoms in fluorophenylborates, particularly at the para-position relative to the boron atom, with bulky groups with a view to increasing the solubility of the activator in the aliphatic solvents typically used in solution polymerization processes and to increasing the molecular weight of the resultant polymers. For example, in *J. Am. Chem. Soc.* 1998, 120, page 6287, Chen et al. disclose substituting the para fluorine with a —Si(t-Bu)$_2$Me group or —Si(i-Pr)$_3$ group, whereas substitution, again at the para-position, with an —OSi(i-Pr)$_3$ group is proposed in U.S. Pat. No. 6,541,410. International Patent Publication No. WO 01/81435 discloses para-substitution with an —N(R)(C$_6$F$_5$) moiety, where R can be methyl, whereas para-substitution with a —C$_6$F$_5$ moiety is proposed in Japanese Published Patent Application No. 9-15892 and with a —CF(C$_6$F$_5$)$_2$ moiety is proposed in *J. Am. Chem. Soc.* 2000, 122, page 1832.

To date, however, little or no attention has been paid to substitution at the meta positions on the phenyl groups of fluorophenylborates.

SUMMARY

Accordingly, the invention resides in one aspect in a fluorophenylborate useful as an activator for an olefin polymerization catalyst, the fluorophenylborate being represented by the formula:

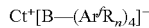

$$Ct^+[B-(Ar^fR_n)_4]^-$$

where Ct$^+$ is a cation capable of extracting an alkyl group from, or breaking a carbon-metal bond of, an organo metallic compound; Ar$^f$ is a fluorophenyl group; n is 1 or 2; and each R is independently selected from a fluorophenyl group and a fluoronaphthyl group, provided that when n=1, each R group is connected at the 3-position relative the connection between the associated Ar$^f$ group and the boron atom and, when n=2; the R groups are connected at the 3-position and the 5-position respectively relative the connection between the associated Ar$^f$ group and the boron atom.

Conveniently, each R is independently selected from a perfluorophenyl group and a perfluoronaphthyl group.

In one embodiment, each Ar$^f$ is a perfluorophenyl group.

Conveniently, Ct$^+$ is selected from silylium, trityl carbenium, Group-12 metal, anilinium, ammonium, phosphonium, and arsonium cations, and anilinium, ammonium, phosphonium, and arsonium cationic derivatives wherein the cationic derivatives contain C$_1$ to C$_8$ hydrocarbyl, hydrocarbylsilyl, or hydrocarbyl-amine substituents for one or more cation hydrogen atoms. In one preferred embodiment, Ct$^+$ is a [4-t-butyl-N,N-dimethylanilinium] cation.

In a further aspect, the invention resides in an olefin polymerization catalyst system comprising (a) a catalyst precursor comprising an organometallic compound and (b) an activator comprising a compound represented by the formula:

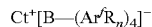

$$Ct^+[B-(Ar^fR_n)_4]^-$$

where Ct$^+$ is a cation capable of extracting an alkyl group from, or breaking a carbon-metal bond of, an organo metallic compound; Ar$^f$ is a fluorophenyl group; n is 1 or 2; and each R is independently selected from a fluorophenyl group and a fluoronaphthyl group, provided that when n=1, each R group is connected at the 3-position relative the connection between the associated Ar$^f$ group and the boron atom and, when n=2; the R groups are connected at the 3-position and the 5-position respectively relative the connection between the associated Ar$^f$ group and the boron atom.

Conveniently, said catalyst precursor is selected from a metallocene catalyst precursor, a bisamide catalyst precursor, an amine bisamide catalyst precursor, or a pyridine bisamide catalyst precursor.

In yet a further aspect, the invention resides in a process for polymerizing at least one olefin monomer in the presence of a catalyst system according to said further aspect of the invention.

DETAILED DESCRIPTION

For the purposes of this invention and the claims thereto, when a polymer is referred to as comprising a monomer, the monomer present in the polymer is the polymerized form of the monomer. Likewise when catalyst components are described as comprising neutral stable forms of the components, it is well understood by one of ordinary skill in the art, that the active form of the component is the form that reacts with the monomers to produce polymers. In addition, a reactor is any container(s) in which a chemical reaction occurs.

For the purposes of this invention and the claims thereto, the new numbering scheme for the Periodic Table Groups is used as described in CHEMICAL AND ENGINEERING NEWS, 63(5), 27 (1985).

The term "catalyst system" is defined to mean a catalyst precursor/activator pair. When "catalyst system" is used to describe such a pair before activation, it means the unactivated catalyst (precatalyst) together with an activator and, optionally, a co-activator. When it is used to describe such a pair after activation, it means the activated catalyst and the activator or other charge-balancing moiety.

The term "catalyst precursor" is also often referred to as precatalyst, catalyst, catalyst precursor, catalyst compound, transition metal compound, metallocene complex, and/or transition metal complex. These words are used interchangeably. Activator and cocatalyst are also used interchangeably. A scavenger is a compound that is typically added to facilitate oligomerization or polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound. The transition metal compound may be neutral as in a precatalyst, or a charged species with a counterion as in an activated catalyst system.

For purposes of this disclosure, the term "fluorophenyl group" means a phenyl group in which at least one hydrogen atom has been replaced by fluorine and is intended to include phenyl compounds in which other hydrogen atoms on the aromatic ring have been replaced by other substituents, such as a hydrocarbyl substituent. The term "perfluorophenyl group" means that each phenyl hydrogen atom has been replaced by a fluorine atom except, in the case of the $Ar^f$ group, the or each hydrogen atom that has been replaced by an R group.

Similarly, the term "fluoronaphthyl group" means a naphthyl group in which at least one hydrogen atom has been replaced by fluorine and is intended to include naphthyl compounds in which other hydrogen atoms on the aromatic ring have been replaced by other substituents, such as a hydrocarbyl substituent. The term "perfluoronaphthyl group" means that each naphthyl hydrogen atom has been replaced by a fluorine atom.

The terms "hydrocarbyl radical", "hydrocarbyl" and "hydrocarbyl group" are defined to include any radical that contains carbon and hydrogen and may be linear, branched, or cyclic, and when cyclic, aromatic or non-aromatic, and include a substituted hydrocarbyl radical, as this term is defined below. When referring to a hydrogen substitutent, the terms "hydrogen" and "hydrogen radical" are used interchangeably.

Substituted hydrocarbyl radicals are radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-hydrocarbon atom or group has been inserted within the hydrocarbyl radical, such as —O—, —S—, —Se—, —Te—, —N(R*)—, =N—, —P(R*)—, =P—, —As(R*)—, =As—, —Sb(R*)—=Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic ring structure.

In some embodiments, the hydrocarbyl radical is selected from methyl, ethyl, ethenyl and isomers of propyl, butyl, pentyl, hexyl, heptyl, octyl, propenyl, butenyl, pentenyl, hexenyl, heptenyl, octenyl propynyl, butynyl, pentynyl, hexynyl, heptynyl, octynyl, butadienyl, pentadienyl, hexadienyl, heptadienyl and octadienyl.

Also included are isomers of saturated, partially unsaturated and aromatic cyclic and polycyclic structures wherein the hydrocarbyl radical may additionally be subjected to the types of substitutions described above. Examples include phenyl, methylphenyl, dimethylphenyl, ethylphenyl, benzyl, methylbenzyl, cyclopentyl, cyclopentenyl, cyclohexyl, cyclohexenyl, methylcyclohexyl, cycloheptyl, cycloheptenyl, norbornyl, norbornenyl, adamantyl and the like.

For this disclosure, when a radical is listed, it indicates that radical type and all other radicals formed when that radical type is subjected to the substitutions defined above. Alkyl, alkenyl and alkynyl radicals listed include all isomers including, where appropriate, cyclic isomers. For example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-methyldiphenyl, 3,4-dimethylphenyl, and 3,5-dimethylphenyl.

The term "hydrocarbylsilyl" is used herein to refer to any branched or unbranched, saturated or unsaturated acyclic or acyclic hydrocarbon radical which has 1 to 8 carbon atoms and which has one or more hydrogen atoms replaced by a silicon atom.

The term "hydrocarbyl-amine" is used herein to refer to any branched or unbranched, saturated or unsaturated acyclic or acyclic hydrocarbon radical has one or more hydrogen atoms replaced by an amino group or substituted amino group.

Fluorophenylborate Activator

The present invention provides a novel fluorophenylborate useful as an activator for an olefin polymerization catalyst system and having the formula:

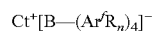

where $Ct^+$ is a cation capable of extracting an alkyl group from, or breaking a carbon-metal bond of, an organo metallic compound; $Ar^f$ is a fluorophenyl group; n is 1 or 2; and each R is independently selected from a fluorophenyl group and a fluoronaphthyl group, provided that when n=1, each R group is connected at the 3-position relative the connection between the associated $Ar^f$ group and the boron atom and, when n=2; the R groups are connected at the 3-position and the 5-position respectively relative the connection between the associated $Ar^f$ group and the boron atom.

Conveniently, each R is independently selected from a perfluorophenyl group and a perfluoronaphthyl group and each $Ar^f$ is a perfluorophenyl group.

Representative compounds according to the invention therefore include the anions:

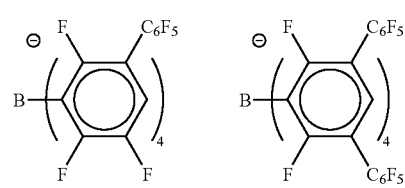

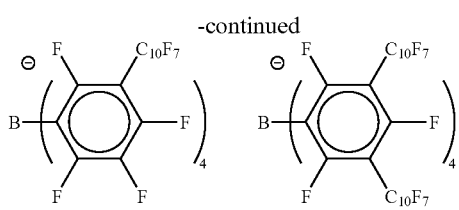

Conveniently, Ct⁺ is selected from silylium, trityl carbenium, Group-12 metal, anilinium, ammonium, phosphonium, and arsonium cations, and anilinium, ammonium, phosphonium, and arsonium cationic derivatives wherein the cationic derivatives contain $C_1$ to $C_8$ hydrocarbyl, hydrocarbylsilyl, or hydrocarbyl-amine substituents for one or more cation hydrogen atoms. In one preferred embodiment, Ct⁺ is a [4-t-butyl-N,N-dimethylanilinium] cation (abbreviated herein as DMAH).

Method of Synthesizing the Fluorophenylborate Activator

The fluorophenylborate of the invention may be prepared by synthetic methods well known in the art. For example, when n=1 and each of R and Ar' is a perfluorophenyl group, one of the bromide substituents in commercially available 1,3-dibromotetrafluorobenzene can readily be replaced by hydrogen by the sequential addition of one equivalent of EtMgBr, followed by an aqueous hydrochloric acid quench. The resulting 3-bromotetrafluorobenzene can then be used to produce 3-pentafluorophenyl-2,4,5,6-tetrafluorobenzene via a copper mediated coupling reaction using, for example, $(C_6F_5)_2Cu$ in dioxane, see Sakamoto et al. *J. Am. Chem. Soc.* 2000, 122, page 1832. The resulting biphenyl can then be converted to the corresponding anilinium borate using standard techniques.

When n=2 and each of R and Ar' is a perfluorophenyl group, synthesis can readily be achieved by initially brominating commercially available 1,3,5-trifluorobenzene to produce the corresponding trifluorotribromobenzene. One of the bromide substituents in the resulting trifluorotribromobenzene can then be replaced by hydrogen by the sequential addition of one equivalent of EtMgBr, followed by an aqueous hydrochloric acid quench. The resulting 3,5-dibromotrifluorobenzene can then used to make 3,5-bis(pentafluorophenyl)trifluorobenzene via a copper mediated coupling reaction. The resultant triphenyl can then be brominated to produce 3,5-bis(pentafluorophenyl)-1-bromotrifluorobenzene, which can then be converted to the corresponding anilinium borate using standard techniques.

Olefin Polymerization Catalyst System

The fluorophenylborate of the invention according to the invention is particularly useful as part of a catalyst system for polymerizing olefins. In such a catalyst system the fluorophenylborate is combined with an organometallic catalyst precursor to perform as an activator to increase the rate at which the catalyst precursor polymerizes olefin monomers and/or to affect the molecular weight, degree of branching, comonomer content or other properties of the resultant polymer.

Organometallic precursors compounds suitable for use with the fluorophenylborate activator of the invention include the known organometallic, transition metal compounds useful in traditional Ziegler-Natta coordination polymerization, particularly the metallocene compounds known to be useful in coordination polymerization. These will typically include Group 3-10 transition metal compounds wherein at least one metal ligand can be abstracted by the cocatalyst activator, particularly those ligands including hydride, hydrocarbyl, and hydrocarbylsilyl, and lower alkyl-substituted ($C_1$ to $C_{10}$) derivatives thereof. Examples include hydride, methyl, benzyl, dimethyl-butadiene, etc. Ligands capable of being abstracted and transition metal compounds comprising them include those metallocenes described in, for example U.S. Pat. No. 5,198,401 and International Patent Publication No. WO 92/00333. Additionally, where the metal ligands include halogen, amido or alkoxy labile ligands (for example, biscyclopentadienyl zirconium dichloride) which do not allow for ready abstraction with the activating cocatalysts of the invention, they can be converted into suitable ligands via known alkylation reactions with organometallic compounds such as lithium or aluminum hydrides or alkyls, alkylalumoxanes, Grignard reagents, etc. See EP 0 500 944 and EP 0 570 982 for the reaction of organoaluminum compounds with dihalo-substituted metallocene compounds prior to addition of activating anion compounds.

Further description of metallocene compounds which comprise, or can be alkylated to comprise, at least one ligand capable of abstraction to form a catalytically active transition metal cation appear in the patent literature, e.g., EP-A-0 129 368, U.S. Pat. Nos. 4,871,705, 4,937,299, 5,324,800, 5,470,993, 5,491,246, 5,512,693, EP-A-0 418 044, EP-A-0 591 756 and International Patent Publication Nos. WO 92/00333, WO 94/01471 and WO 97/22635. Generally, such metallocene compounds comprise mono- or biscyclopentadienyl substituted Group 3, 4, 5, or 6 transition metal compounds wherein the ancillary ligands may be themselves substituted with one or more groups and may be bridged to each other, or may be bridged through a heteroatom to the transition metal. Preferably the cyclopentadienyl rings (including substituted cyclopentadienyl-based fused ring systems, such as indenyl, fluorenyl, azulenyl, or substituted analogs of them), when bridged to each other, will be lower alkyl-substituted ($C_1$ to $C_6$) in the 2 position (with or without a similar 4-position substituent in the fused ring systems) and may additionally comprise alkyl, cycloalkyl, aryl, alkylaryl and or arylalkyl substituents, the latter as linear, branched or cyclic structures including multi-ring structures, for example, those of U.S. Pat. Nos. 5,278,264 and 5,304, 614. Such substituents should each have essentially hydrocarbyl characteristics and will typically contain up to 30 carbon atoms but may be heteroatom containing with 1-5 non-hydrogen/carbon atoms, e.g., N, S, O, P, Ge, B and Si.

Metallocene compounds suitable for the preparation of linear polyethylene or ethylene-containing copolymers (where copolymer means comprising at least two different monomers) are essentially any of those known in the art, see International Patent Publication No. WO 92/00333 and U.S. Pat. Nos. 5,001,205, 5,198,401, 5,324,800, 5,304,614 and 5,308,816, for specific listings. Selection of metallocene compounds for use to make isotactic or syndiotactic polypropylene, and their syntheses, are well-known in the art, specific reference may be made to both patent and academic literature, see for example *Journal of Organometallic Chemistry* 369, 359-370 (1989). Typically those catalysts are stereorigid asymmetric, chiral or bridged chiral metallocenes. See, for example, U.S. Pat. Nos. 4,892,851, 5,017,714, 5,296,434, 5,278,264, International Patent Publication No. WO-A-93/19103, EP-A2-0 577 581, EP-A1-0 578 838, Spaleck et al, *Organometallics* 1994, 13, 954-963, and Brinzinger et al, *Organometallics* 1994, 13, 964-970, and documents referred to therein. Though many of the above are directed to catalyst systems with alumoxane activators, the analogous metallocene compounds will be useful with the cocatalyst activators of this invention for active coordination catalyst systems, when the halogen, amide or alkoxy containing ligands of the metals (where occurring) are replaced with ligands capable of abstraction, for example, via an alkylation reaction as described above, and another is a group into which the ethylene group may insert, for example, hydride, alkyl, alkenyl, or silyl.

Representative metallocene compounds can have the formula:

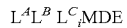

$$L^A L^B L^C_i MDE$$

where, M is a Group 3 to 6 metal; $L^A$ is a substituted or unsubstituted cyclopentadienyl or heterocyclopentadienyl ancillary ligand π-bonded to M; $L^B$ is a member of the class of ancillary ligands defined for $L^A$, or is J, a heteroatom ancillary ligand σ-bonded to M; the $L^A$ and $L^B$ ligands may be covalently bridged together through one or more Group 13 to 16 element-containing linking groups; $L^C_i$ is an optional neutral, non-oxidizing ligand having a dative bond to M (i equals 0 to 3); and, D and E are independently labile ligands, each having a metal-carbon bond to M, optionally bridged to each other or $L^A$ or $L^B$, which bond can be broken for abstraction purposes by a suitable activator and into which a polymerizable monomer or macromonomer can insert for coordination polymerization. Also, the use of hetero-atom containing rings or fused rings, where a non-carbon Group 13, 14, 15 or 16 atom replaces one of the ring carbons is considered for this specification to be within the terms "cyclopentadienyl", "indenyl", and "fluorenyl". See, for example, the International Patent Publication Nos. WO 98/37106 and WO 98/41530. Substituted cyclopentadienyl structures means that one or more hydrogen atoms is replaced with hydrocarbyl, hydrocarbylsilyl, or heteroatom-containing like structures. The hydrocarbyl structures specifically include $C_1$ to $C_{30}$ linear, branched, cyclic alkyl and cycloaromatic fused and pendent rings. These rings may also be substituted with similar structures.

Non-limiting representative metallocene compounds include monocyclopentadienyl compounds such as pentamethylcyclopentadienyltitanium isopropoxide, pentamethylcyclopentadienyltribenzyl titanium, dimethylsilyltetramethylcyclopentadienyl-tert-butylamido titanium dichloride, pentamethylcyclopentadienyl titanium trimethyl, dimethylsilyltetramethylcyclopentadienyl-tert-butylamido zirconium dimethyl, dimethylsilyltetramethylcyclopentadienyl-dodecylamido hafnium dihydride, dimethylsilyltetramethylcyclopentadienyl-dodecylamido hafnium dimethyl, unbridged biscyclopentadienyl compounds such as bis(1,3-butyl, methylcyclopentadienyl)zirconium dimethyl, pentamethylcyclopentadienyl-cyclopentadienyl zirconium dimethyl, (tetramethylcyclopentadienyl)(n-propylcyclopentadienyl) zirconium dimethyl; bridged bis-cyclopentadienyl compounds such as dimethylsilylbis(tetrahydroindenyl)zirconium dichloride and silacyclobutyl(tetramethylcyclopentadienyl)(n-propyl-cyclopentadienyl)zirconium dimethyl; bridged bisindenyl compounds such as dimethylsilylbisindenyl zirconium dichloride, dimethylsilylbisindenyl hafnium dimethyl, dimethylsilylbis(2-methylbenzindenyl) zirconium dichloride, dimethylsilylbis(2-methylbenzindenyl)zirconium dimethyl; and fluorenyl ligand-containing compounds, e.g., diphenylmethyl(fluorenyl)(cyclopentadienyl)zirconium dimethyl; and the additional mono- and biscyclopentadienyl compounds such as those listed and described in U.S. Pat. Nos. 5,017,714 and 5,324,800, International Patent Publication No. WO 92/00333 and EP-A-0 591 756.

Representative traditional Ziegler-Natta transition metal compounds include tetrabenzyl zirconium, tetra bis(trimethylsiylmethyl)zirconium, oxotris(trimethlsilylmethyl)vanadium, tetrabenzyl hafnium, tetrabenzyl titanium, bis(hexamethyldisilazido)dimethyl titanium, tris(trimethylsilylmethyl) niobium dichloride, tris(trimethylsilylmethyl)tantalum dichloride. The important features of such compositions for coordination polymerization are the ligand capable of abstraction and that ligand into which the ethylene (olefinic) group can be inserted. These features enable ligand abstraction from the transition metal compound and the concomitant formation of the ionic catalyst composition of the invention.

Additional organometallic transition metal compounds suitable as olefin polymerization catalysts in accordance with the invention will be any of those Group 3-10 that can be converted by ligand abstraction or σ-bond scission into a catalyticly active cation and stabilized in that active electronic state by a noncoordinating or weakly coordinating anion sufficiently labile to be displaced by an olefinically unsaturated monomer such as ethylene.

Exemplary compounds include those described in International Patent Publications Nos. WO 96/23010 and WO 97/48735 and Gibson et. al., Chem. Comm., pp. 849-850 (1998), which disclose diimine-based ligands for Group 8- to 10 metal compounds shown to be suitable for ionic activation and olefin polymerization. See also WO 97/48735. Transition metal polymerization catalyst systems from Group 5 to 10 metals wherein the active transition metal center is in a high oxidation state and stabilized by low coordination number polyanionic ancillary ligand systems are described in U.S. Pat. Nos. 5,502,124 and 5,504,049. See also the Group 5 organometallic catalyst compounds of U.S. Pat. No. 5,851,945 and the tridentate ligand containing Group 5 to 10 organometallic catalyst compounds of U.S. Pat. No. 6,294,495. Group 11 catalyst precursor compounds, capable of activation with ionizing cocatalysts, useful for olefins and vinyl group-containing polar monomers are described and exemplified in International Patent Publication No. WO 99/30822.

U.S. Pat. No. 5,318,935 describes bridged and unbridged bisamido transition metal catalyst compounds of Group 4 metals capable of insertion polymerization of α-olefins. Bridged bis(arylamido) Group 4 compounds for olefin polymerization are described by McConville et al in Organometallics 1995, 14, 5478-5480. Further work appearing in Macromolecules 1996, 29, 5241-5243 describes bridged bis(arylamido) Group 4 compounds that are active catalysts for polymerization of 1-hexene. Additional transition metal compounds suitable in accordance with the invention include those described in International Patent Publication No. WO 96/40805. Cationic Group 3 or Lanthanide metal complexes for coordination polymerization of olefins are disclosed in International Patent Publication No. WO 00/18808. The precursor metal compounds are stabilized by a monoanionic bidentate ancillary ligand and two monoanionic ligands and are capable of activation with the ionic cocatalysts of the invention.

Additional description of suitable organometallic or organometalloid catalyst precursor compounds may be found in the literature, any of such will be suitable where comprising, or where capable of alkylation to comprise, ligands capable of ionizing abstraction. See, for instance, V. C. Gibson, et al, "The Search for New-Generation Olefin Polymerization Catalysts: Life Beyond Metallocenes", *Angew. Chem. Int. Ed*, 38, 428-447 (1999).

In general, in the catalyst system of the invention the catalyst precursor and the activator are combined in weight ratios of about 10:1 to about 1:10; such as about 5:1 to about 1:5; for example about 2:1 to about 1:2. Multiple activators may be used, including mixtures of alumoxanes with the fluorophenylborate activator of the invention. Alumoxanes are generally oligomeric compounds containing —Al($R^1$)— O— sub-units, where $R^1$ is an alkyl group. Examples of alumoxanes include methylalumoxane (MAO), modified methylalumoxane (MMAO), ethylalumoxane and isobutylalumoxane.

When using the catalyst activator of the invention, the total catalyst system will generally additionally comprise one or more organometallic compound scavenging agents. Such compounds are effective for removing polar impurities from the reaction environment and for increasing catalyst activity. Impurities can be inadvertently introduced with any of the polymerization reaction components, particularly with a solvent, monomer and catalyst feed, and adversely affect catalyst activity and stability. The polar impurities, or catalyst poisons, include water, oxygen and metal impurities. Preferably steps are taken to remove impurities from the polymerization feedstocks before their use, but some minor amounts of organometallic scavenger compound will still normally be used in the polymerization process itself.

Typically these scavenger compounds will be Group 13 organometallic compounds, such as those disclosed in U.S. Pat. Nos. 5,153,157 and 5,241,025 and International Patent Publication Nos. WO 91/09882, WO 94/03506, WO 93/14132 and WO 95/07941. Exemplary compounds include triethyl aluminum, triethyl borane, triisobutyl aluminum, methylalumoxane, and isobutyl aluminumoxane. Those compounds having bulky or $C_6$ to $C_{20}$ linear hydrocarbyl substituents covalently bound to the metal or metalloid center are preferred to minimize adverse interaction with the active catalyst. Examples include triethylaluminum, but more preferably, bulky compounds such as triisobutylaluminum, triisoprenylaluminum, and long-chain linear alkyl-substituted aluminum compounds, such as tri-n-hexylaluminum, tri-n-octylaluminum, or tri-n-dodecylaluminum.

The catalyst system of this invention may also include a support material or carrier. For example, a metallocene complex and one or more activators may be deposited on, contacted with, vaporized with, bonded to, or incorporated within, adsorbed or absorbed in, or on, one or more supports or carriers.

The support material may any of the conventional support materials used in polymerization catalyst systems. Preferably the support material is a porous support material, for example, talc, a zeolite, an inorganic oxide and/or an inorganic chloride. Other support materials include resinous support materials such as polystyrene, functionalized or crosslinked organic supports, such as polystyrene divinyl benzene polyolefins or polymeric compounds, clays, or any other organic or inorganic support material and the like, or mixtures thereof.

The preferred support materials are inorganic oxides that include Group 2, 3, 4, 5, 13 or 14 metal oxides. The preferred supports include silica, which may or may not be dehydrated, fumed silica, alumina (WO 99/60033), silica-alumina and mixtures thereof. Other useful supports include magnesia, titania, zirconia, magnesium chloride (U.S. Pat. No. 5,965,477), montmorillonite (European Patent EP-B1 0 511 665), phyllosilicate and the like. Also, combinations of these support materials may be used, for example, silica-chromium, silica-alumina, silica-titania and the like. Additional support materials may include those porous acrylic polymers described in EP 0 767 184 B1. Other support materials include nanocomposites as described in International Patent Publication No. WO 99/47598, aerogels as described in International Patent Publication No. WO 99/48605, spherulites as described in U.S. Pat. No. 5,972,510 and polymeric beads as described in International Patent Publication No. WO 99/50311.

It is preferred that the support material, most preferably an inorganic oxide, has a surface area in the range of from about 10 to about 700 $m^2/g$, pore volume in the range of from about 0.1 to about 4.0 cc/g and average particle size in the range of from about 5 to about 500 µm. More preferably, the surface area of the support material is in the range of from about 50 to about 500 $m^2/g$, pore volume of from about 0.5 to about 3.5 cc/g and average particle size of from about 10 to about 200 µm. Most preferably the surface area of the support material is in the range is from about 100 to about 400 $m^2/g$, pore volume from about 0.8 to about 3.0 cc/g and average particle size is from about 5 to about 100 µm. The average pore size of the carrier useful in the invention typically has pore size in the range of from about 10 to about 1000 Å, preferably about 50 to about 500 Å, and most preferably about 75 to about 350 Å.

As is well known in the art, the catalyst components, that is the metallocene complex and the activator, may also be supported together on one inert support, or the components may be independently placed on two inert supports and subsequently mixed. Of the two methods, the former is preferred.

In another embodiment the support may comprise one or more types of support material which may be treated differently. For example one could use two different silicas that had different pore volumes or had been calcined at different temperatures. Likewise one could use a silica that had been treated with a scavenger or other additive and a silica that had not.

Monomers

The catalyst system described herein may be used for the polymerization of one or more of monomers. Typical monomers include monomers having from 2 to 30 carbon atoms, preferably 2-12 carbon atoms, and more preferably 2 to 8 carbon atoms. Useful monomers include linear, branched or cyclic olefins, especially linear branched or cyclic alpha-olefins; linear, branched or cyclic diolefins, such as linear branched or cyclic alpha-omega olefins; and linear, branched or cyclic polyenes.

Preferred linear alpha-olefins include $C_2$ to $C_8$ alpha-olefins, more preferably ethylene, propylene, 1-butene, 1-hexene, and 1-octene, even more preferably ethylene, propylene or 1-butene. Preferred branched alpha-olefins include 4-methyl-1-pentene, 3-methyl-1-pentene, and 3,5,5-trimethyl-1-hexene, 5-ethyl-1-nonene. Preferred aromatic-group-containing monomers contain from 7 up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, paramethyl styrene, 4-phenyl-1-butene and allyl benzene.

Non aromatic cyclic group containing monomers can also be used. These monomers can contain from 5 up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, vinylnorbornene, ethylidene norbornene, cyclopentadiene, cyclopentene, cyclohexene, cyclobutene, vinyladamantane and the like.

Diolefin monomers useful in this invention include any hydrocarbon structure, preferably $C_4$ to $C_{30}$, having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

In a preferred embodiment one or more dienes are present in the polymer produced herein at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably 300 ppm or less. In other embodiments at least 50 ppm of diene is added to the polymerization, or 100 ppm or more, or 150 ppm or more.

Preferred monomers include one or more of ethylene, propylene, butene-1, pentene-1,4-methyl-pentene-1, hexene-1, octene-1, decene-1,3-methyl-pentene-1, norbornene, norbornadiene, vinyl norbornene, ethylidene norbornene monomers.

In a particularly preferred embodiment the process of the invention relates to the polymerization of ethylene and at least one comonomer having from 4 to 8 carbon atoms, preferably 4 to 7 carbon atoms. Particularly, the comonomers are butene-1,4-methyl-pentene-1,3-methyl-pentene-1, hexene-1 and octene-1, the most preferred being hexene-1, butene-1 and octene-1.

In another preferred embodiment the polymer produced herein is a propylene homopolymer or copolymer. The comonomer is preferably a $C_4$ to $C_{20}$ linear, branched or cyclic monomer, and in one embodiment is a $C_4$ to $C_{12}$ linear or branched alpha-olefin, preferably butene, pentene, hexene, heptene, octene, nonene, decene, dodecene, 4-methyl-pentene-1,3-methyl pentene-1,3,5,5-trimethyl-hexene-1, and the like. Ethylene may be present at 5 mol % or less.

In another embodiment ethylene or propylene is polymerized with at least two different comonomers to form a terpolymer. The preferred comonomers are a combination of alpha-olefin monomers having 4 to 10 carbon atoms, more preferably 4 to 8 carbon atoms, optionally with at least one diene monomer. The preferred terpolymers include the combinations such as ethylene/butene-1/hexene-1, ethylene/propylene/butene-1, propylene/ethylene/hexene-1, ethylene/propylene/norbornene and the like.

In another embodiment, the olefin polymer comprises:
a first monomer present at from 40 to 95 mole %, preferably 50 to 90 mole %, preferably 60 to 80 mole %, and
a comonomer present at from 5 to 40 mole %, preferably 10 to 60 mole %, more preferably 20 to 40 mole %, and
a termonomer present at from 0 to 10 mole %, more preferably from 0.5 to 5 mole %, more preferably 1 to 3 mole %.

Typically, the first monomer comprises one or more of any $C_3$ to $C_8$ linear, branched or cyclic alpha-olefins, including propylene, butene (and all isomers thereof), pentene (and all isomers thereof), hexene (and all isomers thereof), heptene (and all isomers thereof), and octene (and all isomers thereof). Preferred monomers include propylene, 1-butene, 1-hexene, 1-octene, and the like.

The comonomer may comprise one or more of any $C_2$ to $C_{40}$ linear, branched or cyclic alpha-olefins (provided ethylene, if present, is present at 5 mole % or less), including ethylene, propylene, butene, pentene, hexene, heptene, and octene, nonene, decene, undecene, dodecene, hexadecene, styrene, 3,5,5-trimethylhexene-1,3-methylpentene-1,4-methylpentene-1, norbornene and cyclopentene.

The termonomer may comprise one or more of any $C_2$ to $C_{40}$ linear, branched or cyclic alpha-olefins, (provided ethylene, if present, is present at 5 mole % or less), including, but not limited to, ethylene, propylene, butene, pentene, hexene, heptene, and octene, nonene, decene, undecene, dodecene, hexadecene, butadiene, 1,5-hexadiene, 1,6-heptadiene, 1,4-pentadiene, 1,7-octadiene, 1,8-nonadiene, 1,9-decadiene, 1,11-dodecadiene, styrene, 3,5,5-trimethylhexene-1,3-methylpentene-1,4-methylpentene-1, and cyclopentadiene.

Polymerization Process

The catalyst systems described above are suitable for use in a solution, bulk, gas or slurry polymerization process or a combination thereof, preferably solution phase or bulk phase polymerization process.

One or more reactors in series or in parallel may be used in the polymerization process. Catalyst component and activator may be delivered as a solution or slurry, either separately to the reactor, activated in-line just prior to the reactor, or preactivated and pumped as an activated solution or slurry to the reactor. A preferred operation is two solutions activated in-line. For more information on methods to introduce multiple catalysts into reactors, see U.S. Pat. No.

6,399,722 and International Patent Publication No. WO 01/30862. While these references may emphasize gas phase reactors, the techniques described are equally applicable to other types of reactors, including continuous stirred tank reactors, slurry loop reactors and the like. Polymerizations are carried out in either single reactor operation, in which monomer, comonomers, catalyst/activator, scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors.

In one embodiment 500 ppm or less of hydrogen is added to the polymerization, or 400 ppm or less, or 300 ppm or less. In other embodiments at least 50 ppm of hydrogen is added to the polymerization, or 100 ppm or more, or 150 ppm or more.

Gas Phase Polymerization

Generally, a fluidized gas bed process is used for producing polymers, with a gaseous stream containing one or more monomers being continuously cycled through the fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228.)

Slurry Phase Polymerization

A slurry polymerization process generally operates between 1 to about 50 atmosphere pressure range (15 psi to 735 psi, 103 kPa to 5068 kPa) or even greater and temperatures in the range of 0° C. to about 120° C. In a slurry polymerization, a suspension of solid, particulate polymer is formed in a liquid polymerization diluent medium to which monomer and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

In one embodiment, a preferred polymerization technique useful in the invention is referred to as a particle form polymerization, or a slurry process where the temperature is kept below the temperature at which the polymer goes into solution. Such technique is well known in the art, and described in for instance U.S. Pat. No. 3,248,179. The preferred temperature in the particle form process is within the range of about 85° C. to about 110° C. Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484.

In another embodiment, the slurry process is carried out continuously in a loop reactor. The catalyst, as a slurry in isobutane or as a dry free flowing powder, is injected regularly to the reactor loop, which is itself filled with circulating slurry of growing polymer particles in a diluent of isobutane containing monomer and comonomer. Hydrogen, optionally, may be added as a molecular weight control.

The reactor is maintained at a pressure of 3620 kPa to 4309 kPa and at a temperature in the range of about 60° C. to about 104° C. depending on the desired polymer melting characterisitcs. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In one embodiment of the slurry process useful in the invention the concentration of predominant monomer in the reactor liquid medium is in the range of from about 1 to about 10 weight percent, preferably from about 2 to about 7 weight percent, more preferably from about 2.5 to about 6 weight percent, most preferably from about 3 to about 6 weight percent.

Another process useful in the invention is where the process, preferably a slurry process is operated in the absence of or essentially free of any scavengers, such as triethylaluminum, trimethylaluminum, tri-isobutylaluminum and tri-n-hexylaluminum and diethyl aluminum chloride, dibutyl zinc and the like. This process is described in International Patent Publication No. WO 96/08520 and U.S. Pat. No. 5,712,352.

In another embodiment the process is run with scavengers. Typical scavengers include trimethyl aluminum, tri-isobutyl aluminum and an excess of alumoxane or modified alumoxane.

Homgeneous, Bulk, or Solution Phase Polymerization

The catalysts described herein can be used advantageously in homogeneous solution processes. Generally this involves polymerization in a continuous reactor in which the polymer formed and the starting monomer and catalyst materials supplied, are agitated to reduce or avoid concentration gradients. Suitable processes operate above the melting point of the polymers at high pressures, from 1 to 3000 bar (10-30,000 MPa), in which the monomer acts as diluent or in solution polymerization using a solvent.

Temperature control in the reactor is obtained by balancing the heat of polymerization with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds may also be used. The reactor temperature depends on the catalyst used. In general, the reactor temperature preferably can vary between about 30° C. and about 160° C., more preferably from about 90° C. to about 150° C., and most preferably from about 100° C. to about 140° C. Polymerization temperature may vary depending on catalyst choice. For example a diimine Ni catalyst may be used at 40° C., while a metallocene Ti catalyst can be used at 100° C. or more. In series operation, the second reactor temperature is preferably higher than the first reactor temperature. In parallel reactor operation, the temperatures of the two reactors are independent. The pressure can vary from about 1 mm Hg to 2500 bar (25,000 MPa), preferably from 0.1 bar to 1600 bar (1-16,000 MPa), most preferably from 1.0 to 500 bar (10-5000 MPa).

Each of these processes may also be employed in single reactor, parallel or series reactor configurations. The liquid processes comprise contacting olefin monomers with the above described catalyst system in a suitable diluent or solvent and allowing said monomers to react for a sufficient time to produce the desired polymers. Hydrocarbon solvents are suitable, both aliphatic and aromatic. Alkanes, such as hexane, pentane, isopentane, and octane, are preferred.

The process can be carried out in a continuous stirred tank reactor, batch reactor or plug flow reactor, or more than one reactor operated in series or parallel. These reactors may have or may not have internal cooling or heating and the monomer feed may or may not be refrigerated. See the disclosure of U.S. Pat. No. 5,001,205 for general process conditions. See also, International Patent Publication Nos. WO 96/33227 and WO 97/22639.

This invention also relates to:

1. A fluorophenylborate represented by the formula:

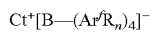

Ct$^+$[B—(Ar$^f$R$_n$)$_4$]$^-$ where Ct$^+$ is a cation capable of extracting an alkyl group from, or breaking a carbon-metal bond of, an organo metallic compound; Ar$^f$ is a fluorophenyl group; n is 1 or 2; and each R is independently selected from a fluorophenyl group and a fluoronaphthyl group, provided that when n=1, each R group is connected at the 3-position relative the connection between the associated Ar$^f$ group and the boron atom and, when n=2; the R groups are connected at the 3-position and the 5-position respectively relative the connection between the associated Ar$^f$ group and the boron atom.

2. The fluorophenylborate of paragraph 1 wherein each R is independently selected from a perfluorophenyl group and a perfluoronaphthyl group.

3. The fluorophenylborate of paragraph 1 or 2 wherein each Ar$^f$ is a perfluorophenyl group.

4. The fluorophenylborate of paragraph 1, 2 or 3 wherein Ct$^+$ is selected from silylium, trityl carbenium, Group-12 metal, anilinium, ammonium, phosphonium, and arsonium cations, and anilinium, ammonium, phosphonium, and arsonium cationic derivatives wherein the cationic derivatives contain C$_1$ to C$_8$ hydrocarbyl, hydrocarbylsilyl, or hydrocarbyl-amine substituents for one or more cation hydrogen atoms.

5. The fluorophenylborate of any of paragraphs 1 to 4 wherein Ct$^+$ is a [4-t-butyl-N,N-dimethylanilini] cation.

6. The fluorophenylborate of paragraphs 1 to 5 and comprising an anion selected from (meta-C$_6$F$_5$—C$_6$F$_4$)$_4$B$^-$ and 3,5-(C$_6$F$_5$)$_2$—C$_6$F$_3$)$_4$B$^{31}$ .

7. An olefin polymerization catalyst system comprising a (a) a catalyst precursor comprising an organometallic compound and (b) an activator comprising a compound represented by the formula:

Ct$^+$[B—(Ar$^f$R$_n$)$_4$]$^-$ where Ct$^+$ is a cation capable of extracting an alkyl group from, or breaking a carbon-metal bond of, an organo metallic compound; Ar$^f$ is a fluorophenyl group; n is 1 or 2; and each R is independently selected from a fluorophenyl group and a fluoronaphthyl group, provided that when n=1, each R group is connected at the 3-position relative the connection between the associated Ar$^f$ group and the boron atom and, when n=2; the R groups are connected at the 3-position and the 5-position respectively relative the connection between the associated Ar$^f$ group and the boron atom.

8. The catalyst system of paragraph 7 wherein each R is independently selected from a perfluorophenyl group and a perfluoronaphthyl group.

9. The catalyst system of paragraph 7 or 8 wherein each Ar$^f$ is a perfluorophenyl group.

10. The catalyst system of paragraph 7, 8, or 9 wherein Ct$^+$ is selected from silylium, trityl carbenium, Group 12 metal, anilinium, ammonium, phosphonium, and arsonium cations, and anilinium, ammonium, phosphonium, and arsonium cationic derivatives wherein the cationic derivatives contain C$_1$ to C$_8$ hydrocarbyl, hydrocarbylsilyl, or hydrocarbyl-amine substituents for one or more cation hydrogen atoms.

11. The catalyst system of paragraph 7, 8, 9, or 10 wherein Ct$^+$ is a [4-t-butyl-N,N-dimethylanilinium] cation.

12. The catalyst system of paragraph 7, 8, 9, 10, or 11 wherein said activator (b) comprises an anion selected from (meta-C$_6$F$_5$—C$_6$F$_4$)$_4$B$^-$ and 3,5-(C$_6$F$_5$)$_2$—C$_6$F$_3$)$_4$B$^-$.

13. The catalyst system of paragraph 7, 8, 9, 10, 11, or 12 wherein said catalyst precursor is selected from a metallocene catalyst precursor, a bisamide catalyst precursor, an amine bisamide catalyst precursor, or a pyridine bisamide catalyst precursor.

14. The catalyst system of paragraph 7, 8, 9, 10, 11, 12, or 13 wherein the catalyst precursor (a) and the activator (b) are present in a ratio of about 10:1 to about 1:10.

15. The catalyst system of paragraph 7, 8, 9, 10, 11, 12, 13, or 14 wherein the catalyst precursor (a) and the activator (b) are present in a ratio of about 5:1 to about 1:5.

16. The catalyst system of any of paragraphs 7 to 15 wherein the catalyst precursor (a) and the activator (b) are present in a ratio of about 2:1 to about 1:2.

17. The catalyst system of any of paragraphs 7 to 16 and further including a porous support.

18. A process for polymerizing at least one olefin monomer comprising contacting said monomer with the catalyst system of any of paragraphs 1 to 17.

19. The process of paragraph 18 wherein said olefin monomer comprises at least one of a C$_2$ to C$_{30}$ olefin, a C$_4$ to C$_{30}$ diolefin, C$_7$ to C$_{30}$ vinyl aromatic monomer and a C$_5$ to C$_{20}$ cyclic olefin.

The process of pargraph 18 wherein said olefin monomer comprises ethylene and/or propylene.

The invention will now be more particularly described with reference to the following non-limiting Examples.

ACTIVATOR SYNTHESIS EXAMPLES

Example 1

Synthesis of 3-Bromotetrafluorobenzene

To a cold (-78° C.) solution of 3,5-tetrabromobenzene (19 grams) in diethyl ether (Et$_2$O) was added BuLi (10 ml, 1.6 M, Aldrich). After 1 hour of reaction time, the mixture was quenched with an HCl(aq)/Et$_2$O mixture and allowed to reach room temperature. The organic layer was separated and dried with MgSO$_4$. The solvent was removed and the product purified by distillation (b.p. 130-135° C., 10.01 grams). $^{19}$F NMR (25° C., CDCl$_3$, referenced with CFCl$_3$) –190.4 (t, 1F), –124.7(m, 1F), –132.6(m, 1F), –162.2(m, 1F).

Example 2

Synthesis of
3-pentafluorophenyl-2,4,5,6-tetrafluorobenzene

To a toluene/tetrahydrofuran solution of the 3-bromotetrafluorobenzene (6 grams) produced in Example 1 was added $(C_6F_5)_2$Cu-dioxane (13 grams) and the mixture was refluxed for 2 days. After an aqueous work-up, the organic layer was separated, and the solvent removed. The residual material was sublimed and the sublimate was passed through a silica column (hexanes). The yield was 5.3 grams. $^{19}$F NMR (25° C., CDCl$_3$, referenced with CFCl$_3$): −114.0 (m, 1F), −128.6 (m, 1F), −130.5 (m, 1F), −138.4(m, 2F), −151.7 (t, 1F), −161.7 (m, 2F), −164.0 (m, 1 F).

Example 3

Synthesis of [4-tBu-PhNMe$_2$H][(m-C$_6$F$_5$—C$_6$F$_4$)$_4$B]

The biphenyl prepared Example 2 was used to make the corresponding borate using standard methodology. To a cold solution of m-C$_6$F$_5$—C$_6$F$_4$H (1.5 grams) in diethylether was added 1 equivalent of BuLi (1.6 M, Aldrich). The reaction was allowed to stir at −78° C. for 1 hour and then a hexane solution of BCl$_3$ (¼equivalent) was added. The ice bath was removed and the reaction mixture was stirred for 3 hours. The solvent was replaced with methylene chloride, and the LiCl byproduct removed. An oily material was obtained after the solvent was removed. Salt metathesis with 4-tBu-PhNMe$_2$HCl was performed using the oily material, and the LiCl byproduct removed by filtration. The solvent was removed under vacuum. The resulting white product was collected. Yield: 1.53 grams. $^{19}$F NMR: −105.5 (bm, 4F), −123.6 (bm, 4F), −139.2 (bm, 8F), −141.5 (bm, 4F), −155.2 (bm, 4F), −163.7 (bm 8F), −169.7 (bm, 4F).

Example 4

Synthesis of 1,3,5-tribromotrifluorobenzene

To a suspension of iron in 1,3,5-trifluorobenzene (40 grams) was added Br$_2$ through a dropping funnel. After the addition was complete, the reaction mixture was refluxed for 16 hours. The mixture was then quenched with an aqueous hydrogen bisulfate solution, and the product extracted with methylene chloride. The organic layer was separated and dried with MgSO$_4$. After filtration, the solvent was removed, leaving a white crystalline material. Yield: 65 grams. $^{19}$F NMR (25° C., CDCl$_3$) −95.9(s).

Example 5

Synthesis of 3,5-dibromotrifluorobenzene 22.363 grams of the Br$_3$F$_3$C$_6$ produced in Example 4 was dissolved in tetrahydrofuran and, after cooling the resultant solution with an ice bath to −5° C., 1 equivalent of EtMgBr (Et$_2$O, Aldrich) was added. A white precipitate appeared after the addition was complete. After stirring the reaction mixture for 1 hour, the ice bath was removed and the temperature was allowed to reach 25° C. After an aqueous work-up, the solvent was evaporated to produce a colorless semisolid material. Yield 10.34 grams. $^{19}$F NMR (25° C., CDCl$_3$) −98.5 (s, 1F), −106.4 (m, 2F).

Example 6

Synthesis of
3,5-bis(pentafluorophenyl)trifluorobenzene

To a toluene/tetrahydrofuran solution of the 3,5-dibromotrifluorobenzene (7.645 grams) produced in Example 5 was added $(C_6F_5)_2$Cu-dioxane (40.0 grams). The mixture was refluxed for 2 days. After an aqueous work-up, the organic layer was separated, and the solvent removed. The residual material was purified by recrystallization from hexane. The product was collected by filtration. Yield 9.64 grams. $^{19}$F NMR (25° C., CDCl$_3$, referenced with CFCl$_3$) −103.9 (s, 2F), −106.3 (s, 1F), −138.1 (m, 4F), −151.5 (t, 2F), −161.5 (m, 4F).

Example 7

Bromination of
3,5-bis(pentafluorophenyl)trifluorobenzene

To a mixture of 3,5-bis(pentafluorophenyl)trifluorobenzene (7.55 grams) produced in Example 6 and iron powder was added Br$_2$. The mixture was refluxed for 3 days. After quenching the Br$_2$ and extracting the product with methylene chloride, the organic layer was dried with MgSO$_4$. After filtering off the drying agent, the solvent was replaced with hexane. Recrystallization afforded the product (5.701 grams) as a white crystalline material.

Example 8

Synthesis of [Li(Et$_2$O$_{2.5}$)][(3,5-(C$_6$F$_5$)$_2$—C$_6$F$_3$)$_4$B]

To a cold solution of 1-bromo-3,5-bis(pentafluorophenyl)trifluorobenzene (5.188 grams) produced in Example 7 was added 1 equivalent of BuLi (1.6M, Aldrich). After 35 minutes, BCl$_3$ was added. The mixture was stirred for 40 minutes, then allowed to reach room temperature, and stirred for an additional 1 hour. The solvent was replaced with methylene chloride and the LiCl removed by filtration using celite. Following partial evaporation, pentane was added to induce precipitation. The mixture was chilled, before the product was collected by filtration. A final pentane wash provided the product as a white solid (3.761 grams). $^{19}$F NMR (25° C., CDCl$_3$, referenced with CFCl$_3$) −95.8 (s, 8F), −118.1 (s, 4F), −139.3 (m, 16F), −155.9 (t, 8F), −164.3 (m, 16F).

Example 9

Synthesis of [4-tBuPhNMe$_2$H][(3,5-(C$_6$F$_5$)$_2$—C$_6$F$_3$)$_4$ B]

3.651 grams of [Li(Et$_2$O$_{2.5}$)][(3,5-(C$_6$F$_5$)$_2$—C$_6$F$_3$)$_4$B] produced in Example 8 were dissolved in methylene chloride and was stirred with a methylene chloride solution of 4-tBuPhNMe$_2$HCl for 45 minutes. The LiCl by-product was removed by filtration. The solvent was replaced with toluene, and pentane added to incipient cloudiness. After chilling the mixture at −35° C., the product was collected by filtration and washed with pentane. The residual solvent was removed by placing the product under high vacuum while heating to 110° C. for 4.5 hours. $^{19}$F NMR (same as Example 3) indicated pure product. Yield: 3.401 grams.

POLYMERIZATION EXAMPLES

A series of ethylene-alpha-olefin copolymerizations were performed using 1-octene as the comonomer and a number of different metallocene catalysts and fluorophenyl and fluoronaphthyl borate activators. The results are reported in Table 1 below.

The activators included the products of Examples 3 and 9 labeled D and B, respectively, in the structural formulae and two conventional borate activators, namely [4-tBuPhNMe$_2$H][(C$_{10}$F$_7$)$_4$B] labeled A in the structural formulae below and [4-tBuPhNMe$_2$H][(C$_6$F$_5$)$_4$B] labeled C in the structural formulae below.

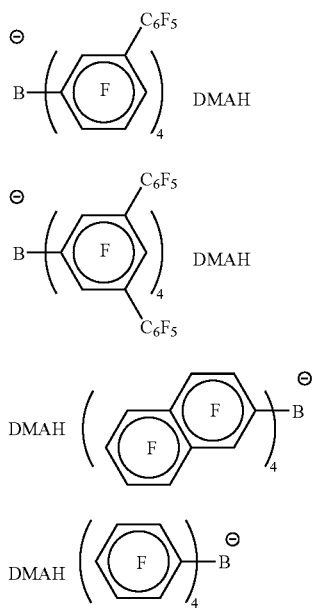

The metallocene catalysts employed included the materials labeled E, F, G, and H in the structural formulae below:

E=bis(para-triethylsilylphenyl)methylene (cyclopentadienyl) (2,7-ditertbutyl-fluorenyl)hafnium dimethyl;

F=dimethylsilyl(bis-indenyl)hafnium dimethyl;

G=dimethylsilyl(tetramethylcyclopentadienyl) (cyclooctylamido)titanium dimethyl; and H=bis(phenyl)methylene(cyclopentadienyl) (fluorenyl) hafnium dimethyl.

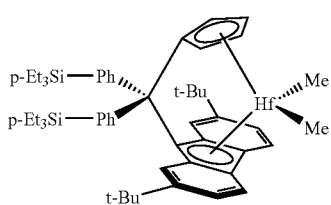

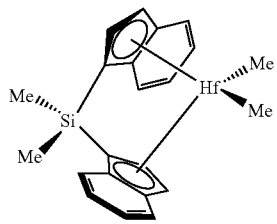

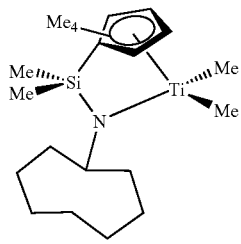

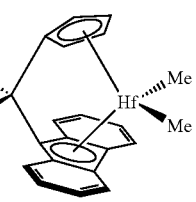

Each polymerization test was run in a glass-lined 5-milliliter autoclave reactor equipped with a mechanical stirrer, an external heater for temperature control, a septum inlet and a regulated supply of dry nitrogen and ethylene in an inert atmosphere (nitrogen) glove box. The reactor was dried and degassed thoroughly at 115° C. A diluent, comonomer, and scavenger, were added at room temperature and atmospheric pressure. The reactor was then brought to process pressure and charged with ethylene while stirring at 800 RPM. The activator and catalyst were added via syringe with the reactor at process conditions. The polymerization was continued while maintaining the reaction vessel within 3° C. of the target process temperature and 5 psig (34 kPa) of target process pressure (by automatic addition of ethylene on demand) until a fixed uptake of ethylene was noted (corresponding to ca. 0.15 g polymer) or until a maximum reaction time of 20 minutes had passed. The reaction was stopped by pressurizing the reactor to 30 psig (207 kPa) above the target process pressure with a gas mixture composed of 5 mol % oxygen in argon. The polymer was recovered by vacuum centrifugation of the reaction mixture. Bulk polymerization activity was calculated by dividing the yield of polymer by the total weight of the catalyst charge by the time in hours and by the absolute monomer pressure in atmospheres. The specific polymerization activity was calculated by dividing the yield of polymer by the total number of millimoles of transition metal contained in the catalyst charge by the time in hours and by the absolute monomer pressure in atmospheres.

TABLE 1

| Activator | Catalyst | % Octene | Mw | Mn | QT(a) | Yield(b) | Act(c) |
|---|---|---|---|---|---|---|---|
| A | E | 30.8 | 873326 | 459306 | 306.9 | 0.209 | 163352 |
| B | E | 26.8 | 1227178 | 389298 | 138.7 | 0.194 | 335886 |
| C | E | 32.6 | 941435 | 359464 | 158.9 | 0.206 | 310403 |
| A | E | 27.8 | 1277730 | 564718 | 222.6 | 0.204 | 219838 |
| B | E | 27.9 | 1306600 | 380611 | 135.2 | 0.182 | 323883 |
| C | E | 28.4 | 917325 | 318875 | 130.9 | 0.203 | 371911 |
| A | F | 24.9 | 538394 | 322048 | 36.7 | 0.113 | 736698 |
| B | F | 27.5 | 345581 | 136350 | 29.6 | 0.184 | 1495135 |
| C | F | 25.6 | 388091 | 231445 | 29.5 | 0.102 | 831707 |
| A | F | 24.7 | 519868 | 305263 | 38.4 | 0.124 | 776067 |
| B | F | 27.2 | 331338 | 126762 | 23.4 | 0.181 | 1862671 |
| C | F | 25.8 | 317877 | 183436 | 25.1 | 0.112 | 1066135 |
| A | G | 32.8 | 529095 | 248672 | 54.7 | 0.155 | 680132 |
| B | G | 34.0 | 727898 | 199555 | 61.9 | 0.183 | 708686 |
| C | G | 29.2 | 481970 | 236278 | 36.7 | 0.153 | 996843 |
| A | G | 29.8 | 541922 | 249355 | 53.1 | 0.154 | 697270 |
| B | G | 22.5 | 678695 | 224801 | 48.7 | 0.176 | 864847 |
| C | G | 11.6 | 393259 | 173766 | 35.2 | 0.164 | 1118910 |
| A | H | 27.8 | 1281727 | 770214 | 63.4 | 0.094 | 353776 |
| B | H | 28.0 | 1017740 | 371580 | 133.2 | 0.169 | 304347 |
| C | H | 26.9 | 1197383 | 733800 | 94.6 | 0.091 | 231325 |
| A | H | 28.0 | 1330405 | 793966 | 75.3 | 0.105 | 334528 |
| B | H | 26.4 | 1005842 | 367618 | 45.7 | 0.166 | 871582 |
| C | H | 27.1 | 985666 | 552501 | 78.3 | 0.121 | 369655 |
| A | E | 31.9 | 1139206 | 528162 | 159.6 | 0.165 | 247669 |
| B | E | 27.7 | 1297955 | 369483 | 121.4 | 0.184 | 363756 |
| C | E | 31.3 | 1077142 | 391479 | 137.5 | 0.194 | 338370 |
| A | E | 27.5 | 1406540 | 605749 | 143.3 | 0.164 | 275281 |
| B | E | 26.5 | 1261551 | 399811 | 95.8 | 0.176 | 441031 |
| C | E | 32.4 | 1013757 | 489391 | 39.9 | 0.151 | 909100 |
| A | F | 23.1 | 542482 | 324864 | 33.8 | 0.108 | 767830 |
| B | F | 25.1 | 382211 | 157275 | 23.4 | 0.172 | 1756247 |
| C | F | 26.6 | 336457 | 193188 | 26.6 | 0.106 | 955664 |
| A | F | 7.9 | 648240 | 338164 | 7.4 | 0.032 | 1044898 |
| B | F | 20.3 | 326268 | 153321 | 146.1 | 0.374 | 614538 |
| C | F | 25.3 | 335501 | 194869 | 5.7 | 0.093 | 3880139 |
| A | G | 33.6 | 632428 | 290031 | 54.6 | 0.148 | 649350 |
| B | G | 35.0 | 833868 | 276887 | 59.3 | 0.155 | 626298 |
| C | G | 30.5 | 503336 | 248427 | 34.0 | 0.136 | 959154 |
| A | G | 34.0 | 631606 | 329913 | 45.7 | 0.144 | 755517 |
| B | G | 32.8 | 885361 | 400882 | 66.6 | 0.144 | 517167 |
| C | G | 35.5 | 470821 | 231047 | 32.5 | 0.144 | 1064290 |
| A | H | 26.7 | 1513491 | 945792 | 96.2 | 0.086 | 213555 |
| B | H | 24.1 | 1080331 | 451270 | 35.3 | 0.150 | 1020034 |
| C | H | 26.8 | 1503997 | 965301 | 94.5 | 0.064 | 162979 |
| A | H | 28.3 | 1416014 | 905129 | 62.1 | 0.101 | 391750 |
| B | H | 22.6 | 1196811 | 566381 | 76.8 | 0.140 | 438666 |
| C | H | 25.4 | 853983 | 434098 | 59.0 | 0.102 | 416684 |
| A | E | 29.4 | 1739067 | 1171641 | 361.2 | 0.156 | 77845 |
| D | E | 34.5 | 791000 | 203509 | 140.0 | 0.222 | 285604 |
| C | E | 30.9 | 880288 | 324780 | 164.3 | 0.211 | 231067 |
| A | E | 27.1 | 1114124 | 377003 | 155.4 | 0.202 | 233569 |
| D | E | 29.1 | 891463 | 303781 | 163.8 | 0.210 | 231127 |
| C | E | 32.0 | 826184 | 262797 | 131.7 | 0.212 | 289974 |
| A | F | 28.9 | 434332 | 247590 | 27.9 | 0.140 | 904519 |
| D | F | 29.7 | 223643 | 111971 | 19.2 | 0.155 | 1453846 |
| C | F | 27.2 | 266119 | 143140 | 20.4 | 0.139 | 1219667 |
| A | F | 26.8 | 479632 | 286466 | 35.7 | 0.130 | 656287 |
| D | F | 29.5 | 245276 | 130613 | 20.6 | 0.146 | 1274128 |
| C | F | 25.8 | 326288 | 203926 | 28.0 | 0.100 | 641387 |
| A | G | 28.9 | 497448 | 226962 | 51.7 | 0.163 | 568458 |
| D | G | 26.5 | 407860 | 166429 | 49.1 | 0.184 | 673120 |
| C | G | 35.9 | 388306 | 155568 | 30.8 | 0.162 | 947030 |
| A | G | 30.7 | 516519 | 224971 | 50.4 | 0.162 | 577513 |
| D | G | 34.0 | 651541 | 551572 | 45.6 | 0.173 | 682201 |
| C | G | 31.5 | 424935 | 202725 | 35.3 | 0.148 | 751995 |
| A | H | 27.8 | 933784 | 508402 | 112.1 | 0.136 | 217612 |
| D | H | 32.1 | 705849 | 324346 | 107.7 | 0.157 | 262970 |
| C | H | 32.6 | 923314 | 509265 | 84.3 | 0.110 | 234987 |
| A | H | 30.1 | 1008994 | 589812 | 115.3 | 0.129 | 200642 |
| D | H | 30.0 | 683608 | 292334 | 48.7 | 0.167 | 615887 |
| C | H | 26.3 | 968278 | 553254 | 101.2 | 0.122 | 217794 |
| A | E | 26.6 | 1113206 | 376594 | 130.7 | 0.190 | 261139 |
| D | E | 25.8 | 812604 | 260344 | 131.5 | 0.206 | 281537 |
| C | E | 33.9 | 830389 | 288859 | 51.6 | 0.202 | 704863 |
| A | E | 29.5 | 1086331 | 451706 | 71.6 | 0.173 | 435670 |
| D | E | 33.9 | 754390 | 267926 | 88.7 | 0.205 | 416462 |

TABLE 1-continued

| Activator | Catalyst | % Octene | Mw | Mn | QT(a) | Yield(b) | Act(c) |
|---|---|---|---|---|---|---|---|
| C | E | 31.3 | 864963 | 302902 | 107.7 | 0.198 | 330875 |
| A | F | 27.2 | 440115 | 250287 | 24.9 | 0.140 | 1012953 |
| D | F | 26.0 | 220341 | 107690 | 19.2 | 0.152 | 1427263 |
| C | F | 25.7 | 266261 | 140377 | 19.1 | 0.135 | 1275079 |
| A | F | 27.6 | 428823 | 250452 | 26.8 | 0.123 | 826119 |
| D | F | 27.3 | 260176 | 139289 | 30.7 | 0.154 | 903520 |
| C | F | 27.1 | 275397 | 154858 | 22.2 | 0.126 | 1025553 |
| A | G | 36.3 | 575980 | 222526 | 48.5 | 0.170 | 630538 |
| D | G | 28.1 | 462870 | 213858 | 33.7 | 0.159 | 846902 |
| C | G | 35.6 | 450127 | 227673 | 33.8 | 0.145 | 770668 |
| A | G | 30.3 | 541348 | 243450 | 47.2 | 0.160 | 609413 |
| D | G | 25.5 | 423513 | 169533 | 33.7 | 0.173 | 923747 |
| C | G | 33.6 | 452305 | 215879 | 34.1 | 0.156 | 825330 |
| A | H | 27.5 | 1169360 | 662620 | 102.2 | 0.129 | 226475 |
| D | H | 33.0 | 698392 | 279906 | 51.9 | 0.172 | 598033 |
| C | H | 27.9 | 838232 | 408637 | 50.6 | 0.148 | 526543 |
| A | H | 30.8 | 1133963 | 694364 | 56.3 | 0.118 | 375733 |
| D | H | 30.1 | 765102 | 339351 | 41.4 | 0.157 | 682234 |
| C | H | 28.5 | 841879 | 438440 | 54.6 | 0.135 | 446619 |

(a)QT = Quench Time (sec);
(b)grams;
(c)Act = activity in grams of polymer/(mmol hour).

All documents described herein are incorporated by reference herein, including any priority documents and/or testing procedures. As is apparent from the foregoing general description and the specific embodiments, while forms of the invention have been illustrated and described, various modifications can be made without departing from the spirit and scope of the invention. Accordingly, it is not intended that the invention be limited thereby.

The invention claimed is:

1. A fluorophenylborate represented by the formula:

$$Ct^+[B-(Ar^fR_n)_4]^-$$

where $Ct^+$ is a cation capable of extracting an alkyl group from, or breaking a carbon-metal bond of, an organo metallic compound; $Ar^f$ is a fluorophenyl group; n is 1 or 2; and each R is independently selected from a fluorophenyl group and a fluoronaphthyl group, provided that when n=1, each R group is connected at the 3-position relative the connection between the associated $Ar^f$ group and the boron atom and, when n=2; the R groups are connected at the 3-position and the 5-position respectively relative the connection between the associated $Ar^f$ group and the boron atom.

2. The fluorophenylborate of claim 1 wherein each R is independently selected from a perfluorophenyl group and a perfluoronaphthyl group.

3. The fluorophenylborate of claim 1 wherein each $Ar^f$ is a perfluorophenyl group.

4. The fluorophenylborate of claim 1 wherein $Ct^+$ is selected from silylium, trityl carbenium, Group-12 metal, anilinium, ammonium, phosphonium, and arsonium cations, and anilinium, ammonium, phosphonium, and arsonium cationic derivatives wherein the cationic derivatives contain $C_1$ to $C_8$ hydrocarbyl, hydrocarbylsilyl, or hydrocarbyl-amine substituents for one or more cation hydrogen atoms.

5. The fluorophenylborate of claim 1 wherein $Ct^+$ is a [4-t-butyl-N,N-dimethylanilinium] cation.

6. The fluorophenylborate of claim 1 and comprising an anion selected from (meta-$C_6F_5$—$C_6F_4$)$_4$B$^-$ and 3,5-($C_6F_5$)$_2$—$C_6F_3$)$_4$B$^-$.

7. An olefin polymerization catalyst system comprising a (a) a catalyst precursor comprising an organometallic compound and (b) an activator comprising a compound represented by the formula:

$$Ct^+[B-(Ar^fR_n)_4]^-$$

where $Ct^+$ is a cation capable of extracting an alkyl group from, or breaking a carbon-metal bond of, an organo metallic compound; $Ar^f$ is a fluorophenyl group; n is 1 or 2; and each R is independently selected from a fluorophenyl group and a fluoronaphthyl group, provided that when n=1, each R group is connected at the 3-position relative the connection between the associated $Ar^f$ group and the boron atom and, when n=2; the R groups are connected at the 3-position and the 5-position respectively relative the connection between the associated $Ar^f$ group and the boron atom.

8. The catalyst system of claim 7 wherein each R is independently selected from a perfluorophenyl group and a perfluoronaphthyl group.

9. The catalyst system of claim 7 wherein each $Ar^f$ is a perfluorophenyl group.

10. The catalyst system of claim 7 wherein $Ct^+$ is selected from silylium, trityl carbenium, Group 12 metal, anilinium, ammonium, phosphonium, and arsonium cations, and anilinium, ammonium, phosphonium, and arsonium cationic derivatives wherein the cationic derivatives contain $C_1$ to $C_8$ hydrocarbyl, hydrocarbylsilyl, or hydrocarbyl-amine substituents for one or more cation hydrogen atoms.

11. The catalyst system of claim 7 wherein $Ct^+$ is a [4-t-butyl-N,N-dimethylanilinium] cation.

12. The catalyst system of claim 7 wherein said activator (b) comprises an anion selected from (meta-$C_6F_5$—$C_6F_4$)$_4$B$^-$ and 3,5-($C_6F_5$)$_2$—$C_6F_3$)$_4$B$^-$.

13. The catalyst system of claim 7 wherein said catalyst precursor is selected from a metallocene catalyst precursor, a bisamide catalyst precursor, an amine bisamide catalyst precursor, or a pyridine bisamide catalyst precursor.

14. The catalyst system of claim 7 wherein the catalyst precursor (a) and the activator (b) are present in a ratio of about 10:1 to about 1:10.

15. The catalyst system of claim 7 wherein the catalyst precursor (a) and the activator (b) are present in a ratio of about 5:1 to about 1:5.

16. The catalyst system of claim 7 wherein the catalyst precursor (a) and the activator (b) are present in a ratio of about 2:1 to about 1:2.

17. The catalyst system of claim 7 and further including a porous support.

18. A process for polymerizing at least one olefin monomer comprising contacting said monomer with the catalyst system of claim 7.

19. The process of claim 18 wherein said olefin monomer comprises at least one of a $C_2$ to $C_{30}$ olefin, a $C_4$ to $C_{30}$ diolefin, $C_7$ to $C_{30}$ vinyl aromatic monomer and a $C_5$ to $C_{20}$ cyclic olefin.

20. The process of claim 18 wherein said olefin monomer comprises ethylene and/or propylene.

* * * * *